(12) United States Patent
Yabe et al.

(10) Patent No.: US 8,303,493 B2
(45) Date of Patent: Nov. 6, 2012

(54) LIGHT SOURCE DEVICE AND ENDOSCOPE APPARATUS USING THE SAME

(75) Inventors: Yusuke Yabe, Hachioji (JP); Koji Omori, Hachioji (JP); Shinji Yamashita, Tachikawa (JP); Yoshimine Kobayashi, Hachioji (JP); Masato Toda, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 748 days.

(21) Appl. No.: 12/496,822

(22) Filed: Jul. 2, 2009

(65) Prior Publication Data

US 2010/0002292 A1 Jan. 7, 2010

(30) Foreign Application Priority Data

Jul. 4, 2008 (JP) .................................. 2008-176002

(51) Int. Cl.
*A61B 1/06* (2006.01)
(52) U.S. Cl. .......................... 600/178; 600/181; 362/574
(58) Field of Classification Search .................. 600/178, 600/181; 362/574; 348/68
See application file for complete search history.

(56) References Cited

U.S. PATENT DOCUMENTS

| | | | | |
|---|---|---|---|---|
| 5,749,830 A * | 5/1998 | Kaneko et al. | ................. | 600/160 |
| 6,280,378 B1 * | 8/2001 | Kazuhiro et al. | ............. | 600/160 |
| 6,482,150 B2 * | 11/2002 | Utsui | ............................ | 600/178 |
| 6,635,011 B1 * | 10/2003 | Ozawa et al. | ................. | 600/178 |
| 6,638,215 B2 * | 10/2003 | Kobayashi | ..................... | 600/160 |
| 2002/0042556 A1 * | 4/2002 | Sugimoto et al. | ............. | 600/178 |
| 2003/0139650 A1 * | 7/2003 | Homma | ......................... | 600/181 |
| 2003/0232445 A1 * | 12/2003 | Fulghum, Jr. | ................... | 436/63 |
| 2005/0288556 A1 * | 12/2005 | Sugimoto | ..................... | 600/160 |
| 2008/0249368 A1 * | 10/2008 | Takei | ............................ | 600/178 |

FOREIGN PATENT DOCUMENTS

| | | |
|---|---|---|
| DE | 101 36 419 A1 | 2/2002 |
| EP | 2 036 484 A2 | 3/2009 |
| JP | 2002-336196 | 11/2002 |
| JP | 2007-143647 | 6/2007 |
| JP | 2007-175210 | 7/2007 |

OTHER PUBLICATIONS

Extended European Search Report dated Sep. 29, 2009.

* cited by examiner

*Primary Examiner* — John P Leubecker
(74) *Attorney, Agent, or Firm* — Scully, Scott, Murphy & Presser, PC

(57) ABSTRACT

A switching filter is provided in a light source device. The switching filter has a first dichroic filter which transmits illumination light in a first wavelength band from a lamp and a fluorescence observation filter which transmits at least illumination light in a second wavelength band and is rotatably provided such that the first dichroic filter and the fluorescence observation filter pass through an illumination light optical axis. An LED portion has a blue LED which emits illumination light in the first wavelength band toward the switching filter. A second dichroic filter capable of transmitting illumination light from the lamp and reflecting illumination light from the LED portion to a condenser lens is also arranged at the switching filter.

3 Claims, 8 Drawing Sheets

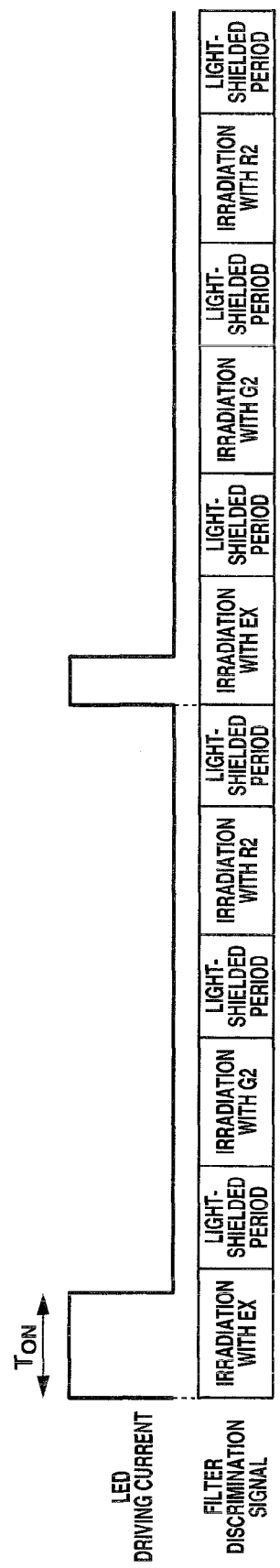

LIGHT SOURCE DEVICE AND ENDOSCOPE APPARATUS USING THE SAME

This application claims benefit of Japanese Application No. 2008-176002 filed in Japan on Jul. 4, 2008, the contents of which are incorporated by this reference.

BACKGROUND OF THE INVENTION

1. Field of the Invention

The present invention relates to a light source device used for normal observation using normal light and fluorescence observation using fluorescence and an endoscope apparatus using the light source device.

2. Description of the Related Art

Examples of observation of living tissue using an endoscope include fluorescence observation, which applies excitation light and performs observation using a fluorescence image, in addition to normal endoscopic observation using visible light (normal light). The fluorescence observation takes advantage of the fact that when light with a wavelength of 400 to 480 nm (excitation light) is applied to living tissue, a normal tissue emits strong fluorescence with a wavelength in the range of about 480 to 630 nm while a diseased part such as a cancerous cell emits weak fluorescence and is known as a technique capable of detecting an abnormal part such as early cancer which is hard to visually recognize by normal endoscopic observation.

A conventional endoscope apparatus for fluorescence observation generates excitation light necessary for fluorescence observation by an excitation light filter which is arranged in an optical path of illumination light emitted from a light source and transmits only excitation light. The endoscope apparatus applies excitation light to living tissue and obtains autofluorescence by a fluorescence transmission filter which is arranged between an objective optical system at a distal end portion of an insertion portion of an endoscope and a solid-state image pickup device and transmits only light with a fluorescence wavelength.

In recent years, endoscope apparatuses capable of normal observation using normal light and fluorescence observation using fluorescence have been proposed. For example, some of the endoscope apparatuses generate, from light from a light source, excitation light through an excitation light filter provided on a rotating filter, apply the excitation light to living tissue, and obtain fluorescence.

For example, Japanese Patent Application Laid-Open Publication No. 2002-336196 discloses a technique related to an endoscope apparatus configured to be capable of switching between a normal image mode and a fluorescence image mode by arranging a switching filter which is a rotating plate in an optical path from a light source and concentrically providing an RGB filter for normal observation and a fluorescence observation filter on an inner peripheral side and an outer peripheral side of the switching filter.

Japanese Patent Application Laid-Open Publication No. 2007-175210 discloses a technique related to an endoscope apparatus which has a lamp and an excitation light unit within a light source device and is configured such that a dichroic mirror for combining optical paths for the lamp and excitation light unit is arranged between a rotating plate and a condensing lens.

Japanese Patent Application Laid-Open Publication No. 2007-143647 discloses a technique related to an endoscope apparatus configured for fluorescence observation to compensate for a deficiency in the amount of excitation light by lighting an excitation light light-emitting device (blue LED) to suit excitation light emitted when white light is filtered through a rotating filter.

SUMMARY OF THE INVENTION

A light source device according to the present invention includes a first light source which emits illumination light whose wavelength band covers a first wavelength band and a second wavelength band, a light condensing portion which is arranged on an optical axis of illumination light emitted from the first light source and condenses light, a rotating plate which has a first window portion that transmits illumination light in the first wavelength band and a second window portion that transmits at least illumination light in the second wavelength band and is rotatably arranged such that the first window portion and the second window portion pass through the optical axis of the illumination light, a driving control portion which controls rotation of the rotating plate, a second light source which emits illumination light in the first wavelength band toward the rotating plate, and an optical device which is arranged at the rotating plate, can transmit the illumination light emitted from the first light source, and can reflect the illumination light emitted from the second light source to the light condensing portion.

An endoscope apparatus according to the present invention includes a light source device including a first light source which emits illumination light whose wavelength band covers a first wavelength band and a second wavelength band, a light condensing portion which is arranged on an optical axis of illumination light emitted from the first light source and condenses light, a rotating plate which has a first window portion that transmits illumination light in the first wavelength band and a second window portion that transmits at least illumination light in the second wavelength band and is rotatably arranged such that the first window portion and the second window portion pass through the optical axis of the illumination light, a driving control portion which controls rotation of the rotating plate, a second light source which emits illumination light in the first wavelength band toward the rotating plate, and an optical device which is arranged at the rotating plate, can transmit the illumination light emitted from the first light source, and can reflect the illumination light emitted from the second light source to the light condensing portion and an endoscope including a distal end portion including an observation optical system which applies light from the condensing portion of the light source device to a subject and an image pickup optical system which picks up an image of the subject, and an insertion portion which is connected to the distal end portion on an insertion direction proximal end side.

BRIEF DESCRIPTION OF THE DRAWINGS

FIG. 13 is a timing chart showing an example of control of the second light source portion by the LED driving portion in FIG. 1 and an example of control of the switching filter by a control portion.

DETAILED DESCRIPTION OF THE PREFERRED EMBODIMENTS

An embodiment of the present invention will be described below with reference to the drawings.

Embodiment

Figure 1:
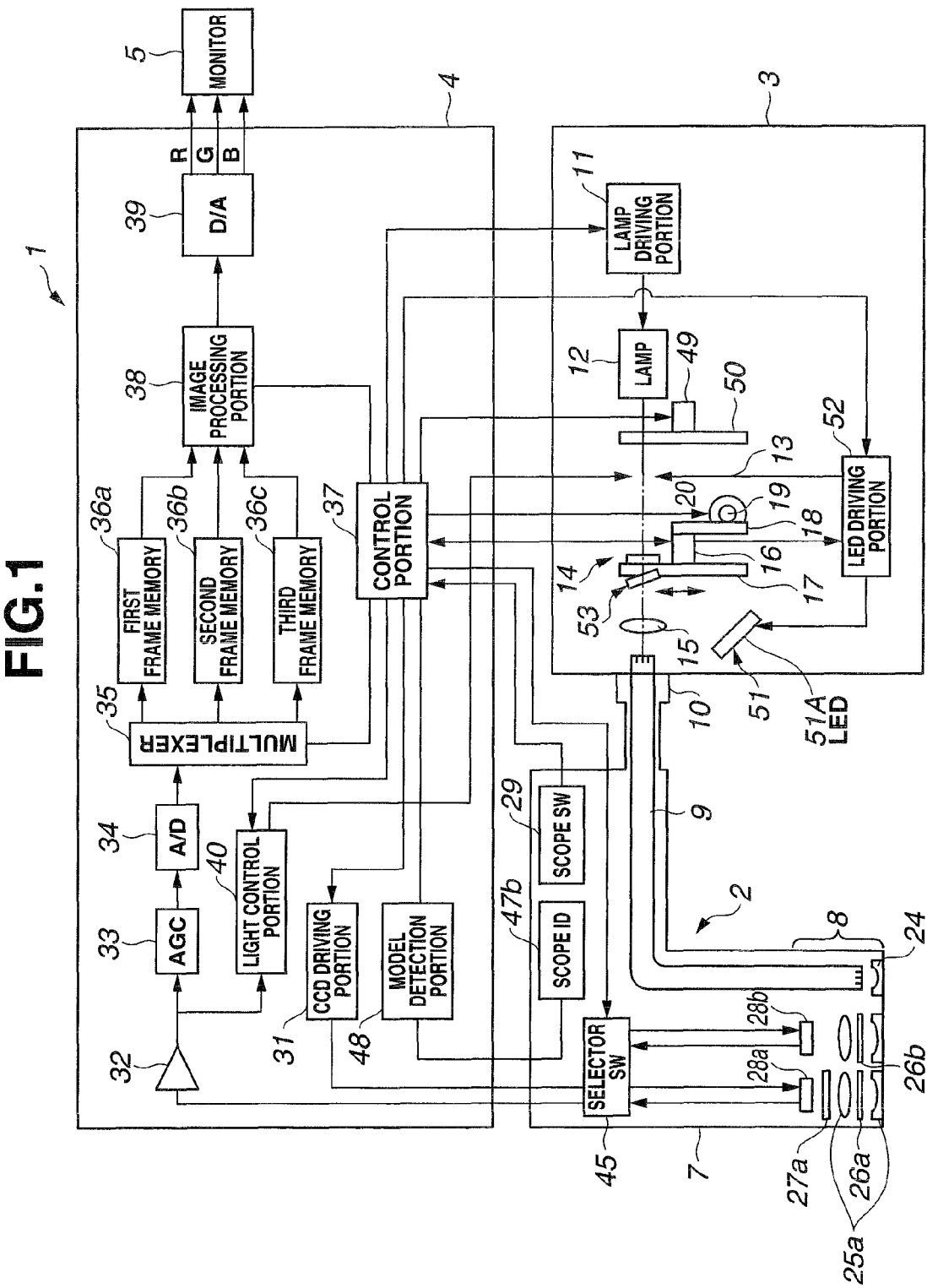
FIG. 1 is a block diagram showing an overall configuration of an endoscope apparatus including a light source device according to a first embodiment of the present invention.
Figure 2:
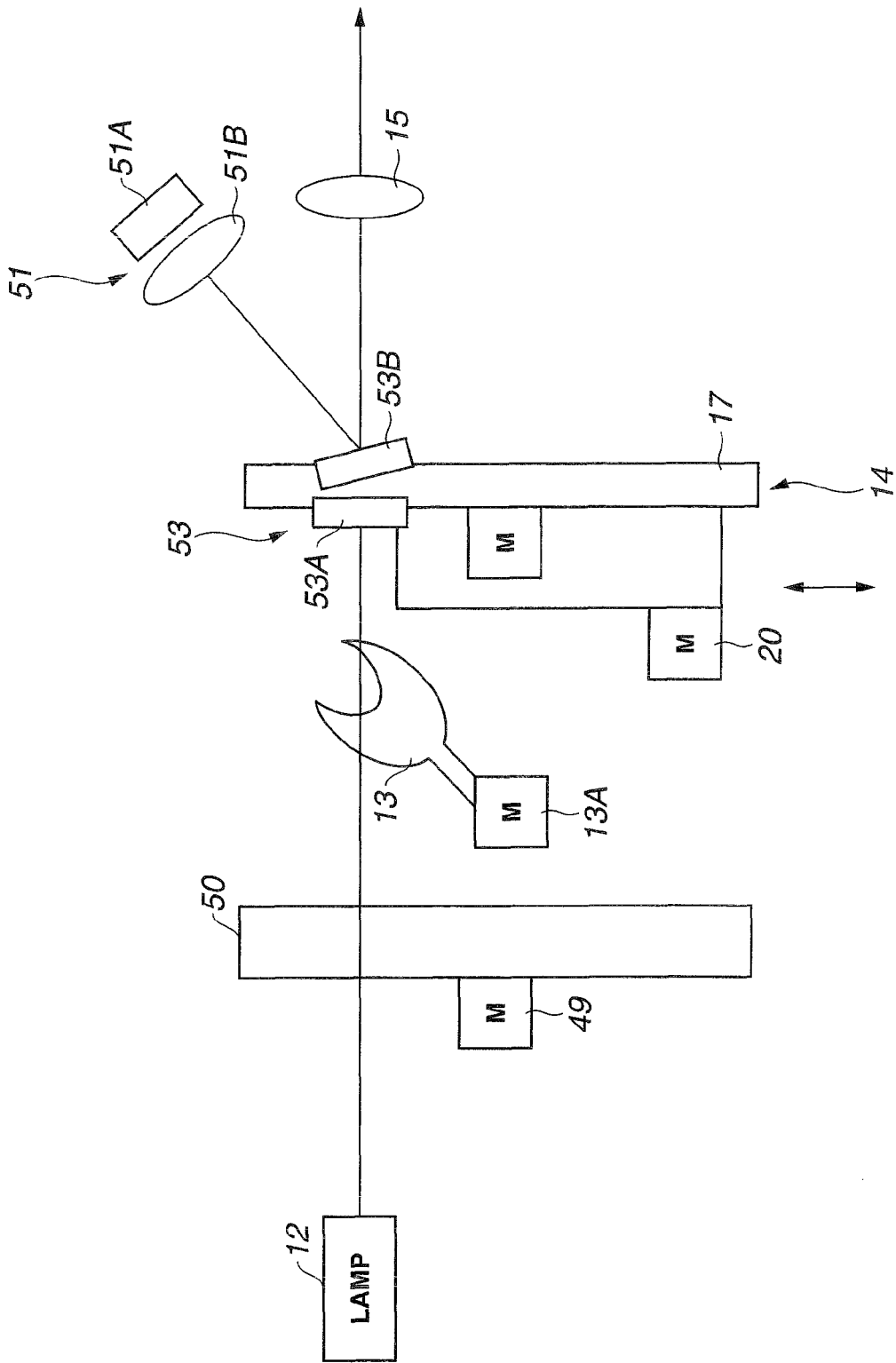
FIG. 2 is a configuration diagram showing a schematic configuration of a main portion of the light source device in FIG. 1.
Figure 3:
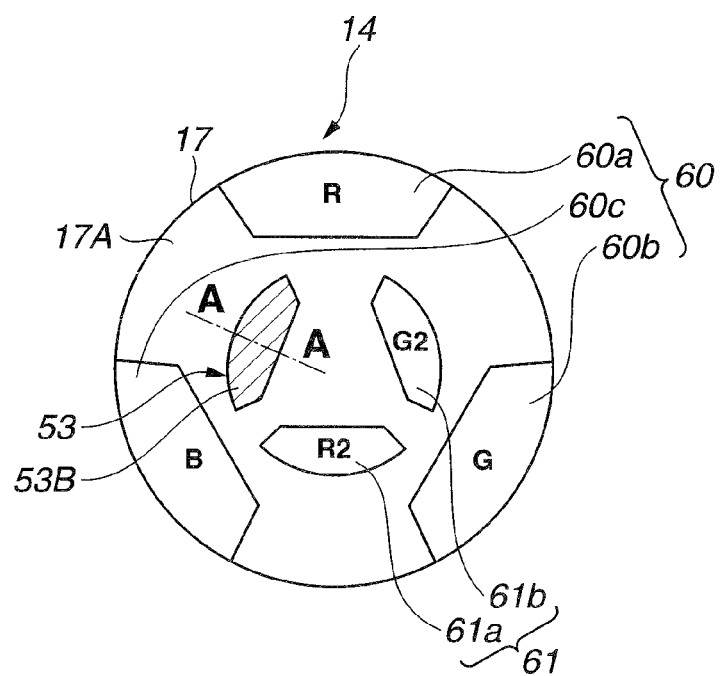
FIG. 3 is a configuration view showing a configuration of a switching filter in which a normal observation filter, a fluorescence observation filter, and a fluorescence observation optical device are provided.
Figure 4:
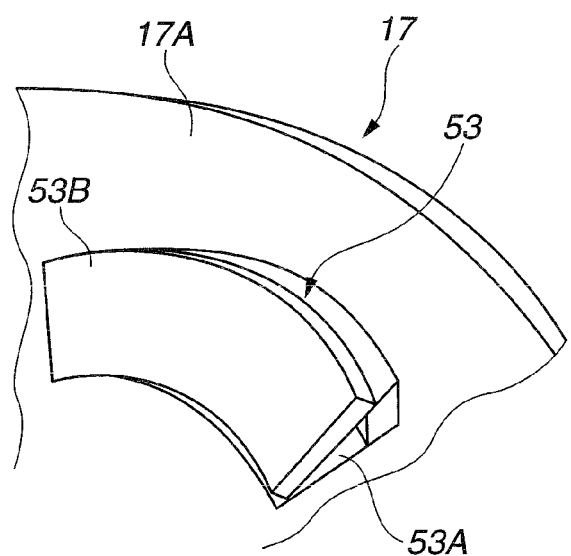
FIG. 4 is a perspective view showing an example of how the fluorescence observation optical device is attached to the switching filter in FIG. 3.
Figure 5:
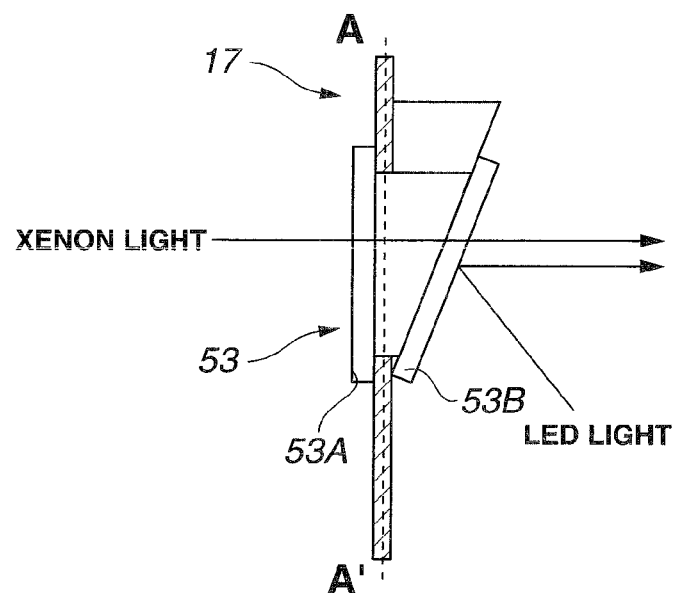
FIG. 5 is a sectional view taken along line A-A in FIG. 3 for explaining how the fluorescence observation optical device is attached.
Figure 6:
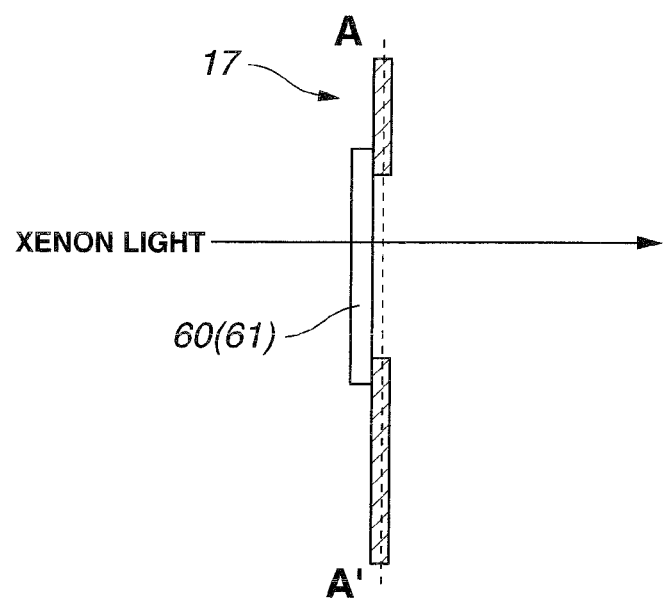
FIG. 6 is a sectional view for explaining how the normal observation filter and fluorescence observation filter are attached.
Figure 7:
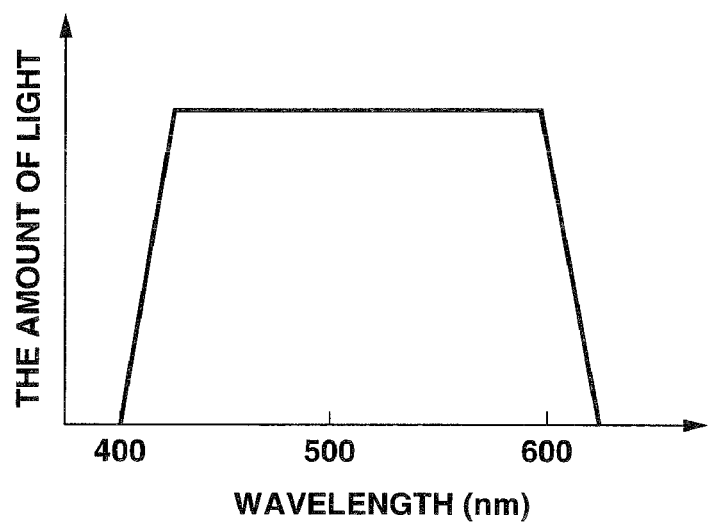
FIG. 7 is a characteristic chart showing a wavelength-light amount characteristic of light applied from a lamp.
Figure 8:
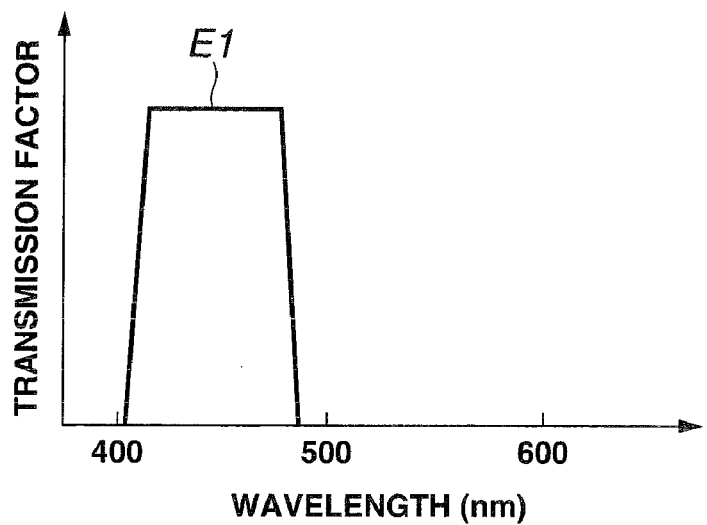
FIG. 8 is a characteristic chart showing a light wavelength-transmission factor characteristic of a first dichroic filter constituting a part of the fluorescence optical device in FIG. 2.
Figure 9:
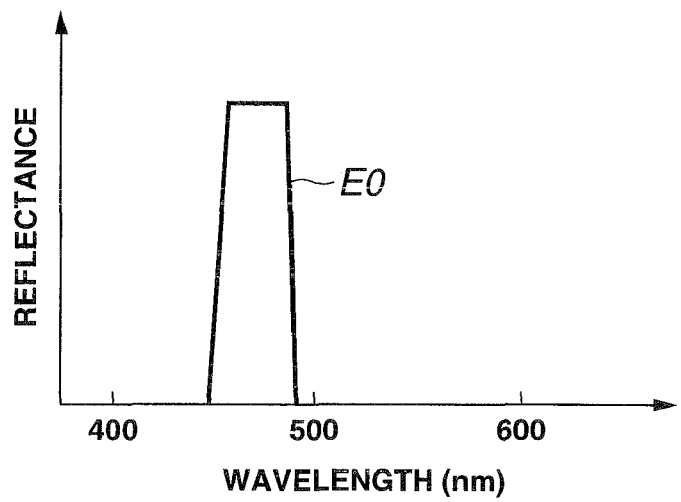
FIG. 9 is a characteristic chart showing a light wavelength-reflectance characteristic of a second dichroic filter constituting a part of the fluorescence optical device in FIG. 2.
Figure 10:
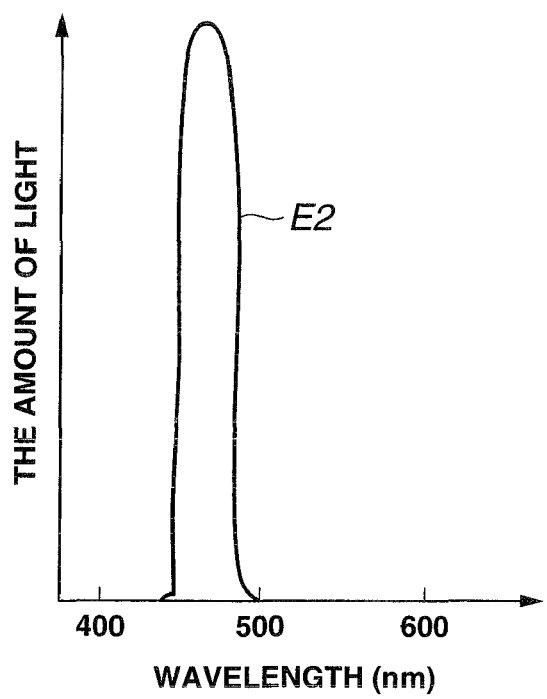
FIG. 10 is a characteristic chart showing a wavelength-light amount characteristic of light (blue light) applied from a second light source portion in FIG. 2.
Figure 11:
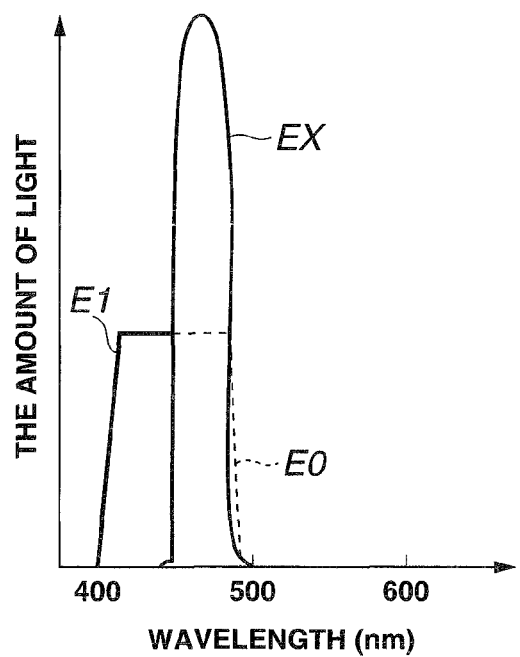
FIG. 11 is a characteristic chart showing a wavelength-light amount characteristic of light condensed by a condenser lens serving as a light condensing portion in FIG. 2.
Figure 12:
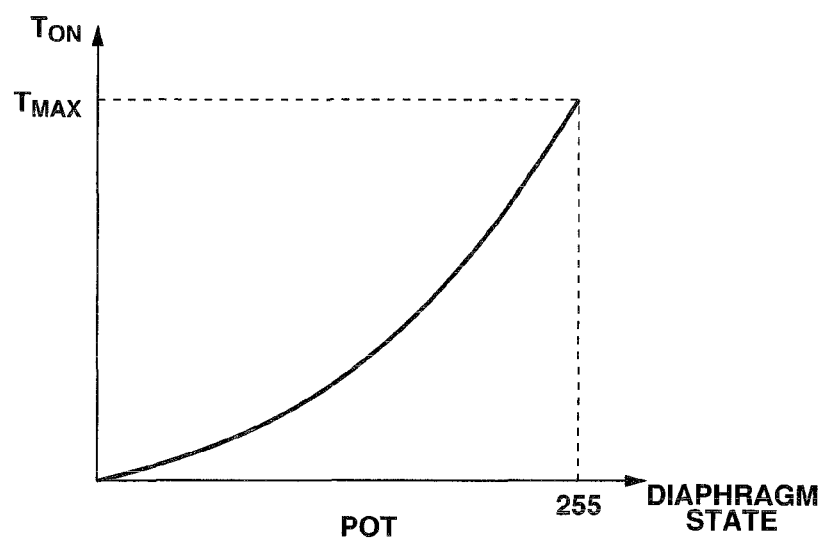
FIG. 12 is a graph showing an example of a lighting time of the second light source portion which varies depending on an open/closed state of a diaphragm determined by an LED driving portion.

FIGS. 1 to 13 relate to an embodiment of the present invention. FIG. 1 is a block diagram showing an overall configuration of an endoscope apparatus including a light source device according to the embodiment. FIG. 2 is a configuration diagram showing a schematic configuration of a main portion of the light source device in FIG. 1. FIG. 3 is a configuration view showing a configuration of a switching filter in which a normal observation filter, a fluorescence observation filter, and a fluorescence observation optical device are provided. FIG. 4 is a perspective view showing an example of how the fluorescence observation optical device is attached to the switching filter in FIG. 3. FIG. 5 is a sectional view taken along line A-A in FIG. 3 for explaining how the fluorescence observation optical device is attached. FIG. 6 is a sectional view for explaining how the normal observation filter and fluorescence observation filter are attached to the switching filter. FIG. 7 is a characteristic chart showing a wavelength-light amount characteristic of light applied from a lamp. FIG. 8 is a characteristic chart showing a light wavelength-transmission factor characteristic of a first dichroic filter constituting a part of the fluorescence optical device in FIG. 2. FIG. 9 is a characteristic chart showing a light wavelength-reflectance characteristic of a second dichroic filter constituting a part of the fluorescence optical device in FIG. 2. FIG. 10 is a characteristic chart showing a wavelength-light amount characteristic of light (blue light) applied from a second light source portion in FIG. 2. FIG. 11 is a characteristic chart showing a wavelength-light amount characteristic of light condensed by a condenser lens serving as a light condensing portion in FIG. 2. FIG. 12 is a graph showing an example of a lighting time of the second light source portion which varies depending on an open/closed state of a diaphragm determined by an LED driving portion. FIG. 13 is a timing chart showing an example of control of the second light source portion by the LED driving portion in FIG. 1 and an example of control of the switching filter by a control portion.

As shown in FIG. 1, an endoscope apparatus 1 including a light source device according to a first embodiment of the present invention is composed of an electronic endoscope (hereinafter simply referred to as an endoscope) 2 which is capable of running in a normal observation mode and in a fluorescence observation mode and is to be inserted into a body cavity for observation, a light source device 3 which emits light for normal observation and light for fluorescence observation, a processor 4 which performs signal processing for forming a normal observation image and a fluorescence image, and a monitor 5 which displays a normal light image and a fluorescence image.

The endoscope 2 has an elongated insertion portion 7 to be inserted into a body cavity and incorporates illumination means and image pickup means at a distal end portion 8 of the insertion portion 7.

A light guide fiber 9 which transmits illumination light for normal observation and excitation light is inserted through the insertion portion 7. A light source connector 10 provided at an incident end on a user's end side of the light guide fiber 9 is detachably connected to the light source device 3 (to be described later).

The endoscope 2 also has a fluorescence observation CCD (fluorescence CCD) 28a and a normal observation CCD (normal CCD) 28b at the distal end portion 8 of the insertion portion 7. Note that CMD (Charged Modulation Device) image pickup devices, C-MOS image pickup devices, AMIs (Amplified MOS Imagers), or BCCDs (Back Illuminated CCDs) may be used as the fluorescence CCD and normal CCD.

A fluorescence observation image pickup portion composed of an objective lens system 25a for forming an optical image, a first diaphragm 26a which spatially limits the amount of light, an excitation light cut-off filter 27a, and a fluorescence CCD 28a as an image pickup device which picks up a fluorescence image and a normal observation image pickup portion composed of an objective lens system 25b for forming an optical image, a second diaphragm 26b, and a normal CCD 28b as an image pickup device which picks up a normal image are arranged at an observation window of the distal end portion 8.

Note that an f-number of the first diaphragm 26a is smaller than an f-number of the second diaphragm 26b. That is, a larger amount of light enters the fluorescence CCD 28a.

The two CCDs 28a and 28b are connected to a CCD driving portion 31 and a preamplifier 32 via a selector switch 45. A switching state of the selector switch 45 is controlled by a control portion 37. That is, when a fluorescence mode is selected by a scope switch 29, the fluorescence CCD 28a is selected and used. On the other hand, when a normal mode is selected, the normal CCD 28b is selected and used.

In the present embodiment, a scope ID circuit 47b which generates unique identification information including the type (model) of a corresponding endoscope is provided for each of the endoscope 2 and an endoscope (not shown) to be used other than the endoscope 2 to allow connection and use of a different type of endoscope (an endoscope other than the endoscope 2).

Note that although each scope ID circuit 47b is composed of a memory device to which information including a model of a corresponding endoscope has been written, the present invention is not limited thereto. For example, the scope ID circuit 47b can be composed of a dip switch made up of a plurality of switches.

A model detection portion 48 for identifying the connected endoscope 2 by identification information is provided on the processor 4 side, and model information detected by the model detection portion 48 is sent to the control portion 37. The control portion 37 controls the light source device 3 and the like according to a detected model such that the endoscope 2 can perform observation in a fluorescence mode and in a normal mode suitable for an endoscope (scope) of the model.

A configuration and characteristics of a main portion of the light source device 3 will be described with reference to FIGS. 1 to 11.

As shown in FIGS. 1 and 2, the light source device 3 has a lamp 12 as a first light source which is driven by a lamp driving portion 11 to emit light and emits light whose wavelength band covers from an infrared wavelength band to a visible light band (light whose wavelength band covers a first wavelength band and a second wavelength band), a light source diaphragm 13 which is provided on an optical path of illumination light from the lamp 12 and limits the amount of light from the lamp 12, a switching filter 50 which is provided between the light source diaphragm 13 and the lamp 12 and whose rotational position is switched by a motor 49, a switching filter portion 14 which is provided on the illumination optical path, a condenser lens 15 constituting a light condensing portion which condenses light having passed through the switching filter portion 14, an LED portion 51 as a second light source which emits light toward the switching filter portion 14, and an LED driving portion 52 which controls the LED portion 51, light source diaphragm 13, switching filter portion 14, and the like.

The lamp 12 is composed of a xenon lamp or the like capable of applying light whose wavelength band covers from the infrared wavelength band to the visible light band (light whose wavelength band covers the first wavelength band and second wavelength band) and has the characteristic of being able to apply light with a wavelength band of about 400 to 630 nm as shown in, e.g., FIG. 7. Note that the lamp 12 is not limited to a xenon lamp which emits the light with the wavelength band, and any other light source capable of applying light with a suitable wavelength band may be used, as needed.

The switching filter 50 has at least one filter which limits a wavelength of excitation light to be applied toward a subject according to the connected and used endoscope 2 in a fluorescence mode, in addition to a filter which actually transmits light without limiting a wavelength band of visible light. The switching filter 50 can be used by switching between the plurality of filters (the filter which does not limit a band and the at least one filter which limits a band) provided at the switching filter 50 according to the scope ID circuit 47b or an observation situation.

The switching filter portion 14 has a switching filter 17 constituting a rotating plate which is rotated by a rotation motor 16 and in which a filter to be arranged on the optical path is switched by a movement motor 20 and the movement motor 20, which moves the switching filter 17 in a direction perpendicular to an optical axis together with the rotation motor 16 by rotationally driving a pinion 19 screwed in a rack 18 attached to the rotation motor 16. Note that the rack 18, pinion 19, and movement motor 20 constitute a movement mechanism.

In the switching filter 17, a fluorescence observation filter 61 and a fluorescence observation optical device 53 constituting a first window portion and a second window portion and an RGB filter 60 for normal observation constituting a third window portion are concentrically provided on an inner peripheral side and on an outer peripheral side, respectively, as shown in FIG. 3.

By driving the movement motor 20, the switching filter 17 can be set to a first position where the fluorescence observation filter 61 and fluorescence observation optical device 53 are located on the optical path and be placed in an operating state in a fluorescence image mode (also referred to as a fluorescence mode) or can be switched from the first position where the fluorescence observation filter 61 and fluorescence observation optical device 53 are located on the optical path to a second position where the normal illumination filter 60 is located on the optical path and can be switched to an operating state in a normal image mode (also referred to as a normal mode).

In the RGB filter 60, an R filter 60a, a G filter 60b, and a B filter 60c which transmit light in a wavelength band for R (red), light in a wavelength band for G (green), and light in a wavelength band for B (blue), respectively, are circumferentially provided at three equally spaced positions. When the RGB filter 60 is rotationally driven by the rotation motor 16, the R filter 60a, G filter 60b, and B filter 60c are sequentially and nearly continuously inserted into the optical path.

Note that the R filter 60a, G filter 60b, and B filter 60c have, as transmission characteristics, the filter characteristics of transmitting light beams in wavelength bands (corresponding to a third wavelength band) of, e.g., 600 to 700 nm, 500 to 600 nm, and 400 to 500 nm, respectively.

In the fluorescence observation filter 61 constituting the second window portion, an R2 filter 61a and a G2 filter 61b which transmit red light (R2) with a narrow band and green light (G2) with a narrow band, respectively, are provided such that the R2 filter 61a, G2 filter 61b, and the fluorescence observation optical device 53 (to be described later) are circumferentially located at three equally spaced positions. When the fluorescence observation filter 61 is rotationally driven by the rotation motor 16, the R2 filter 61a, G2 filter 61b, and the fluorescence observation optical device 53 are sequentially inserted into the optical path.

Note that the R2 filter 61a and G2 filter 61b have, as transmission characteristics, the filter characteristics of transmitting light beams in wavelength bands of, e.g., 640 to 660 nm and 540 to 560 nm, respectively.

In the present embodiment, the fluorescence observation optical device 53 and the LED portion 51 as the second light source are provided to increase the amount of excitation light during running in the fluorescence observation mode, as shown in FIGS. 1 and 2.

The LED portion 51 is configured to have a blue LED 51A and a condensing lens 51B which applies light emitted by the blue LED 51A, as shown in FIG. 2.

The blue LED 51A is a one generally used in a projector or the like and emits, e.g., blue light E2 with a wavelength band which is the first wavelength band, has a center wavelength near 460 nm, and has a bandwidth of 20 nm, as shown in FIG. 10.

The LED portion 51 is fixed within the light source device 3 such that the blue light E2 emitted by the LED portion 51 can be applied toward the fluorescence observation optical device 53 of the switching filter 17 located at the first position, as shown in FIG. 2.

The fluorescence observation optical device 53 constitutes the first window portion and is an optical device capable of transmitting illumination light emitted from the lamp 12 and reflecting blue light (see FIG. 10) emitted from the LED portion 51 to the condenser lens 15, as shown in FIG. 2.

More specifically, the fluorescence observation optical device 53 is configured to have a first dichroic filter 53A which is provided on a light entrance surface of the switching filter 17 and a second dichroic filter 53B which is provided at a predetermined angle on a light exit surface of the switching filter 17 behind the first dichroic filter 53A, as shown in FIGS. 2 to 5.

The first dichroic filter 53A is fixed on the light entrance surface of a rotating plate main body 17A of the switching filter 17 with adhesive or the like, as shown in FIGS. 4 and 5. The second dichroic filter 53B is fixed at the predetermined angle on the light exit surface of the switching filter 17 behind the first dichroic filter 53A via a fixation member.

Note that a method by which the first dichroic filter 53A and second dichroic filter 53B are attached and a structure in which the first dichroic filter 53A and second dichroic filter 53B are attached are not limited to an attachment method and an attachment structure shown in FIG. 5, and another attachment method and another attachment structure may be adopted. The predetermined angle for the second dichroic filter 53B is an angle which allows the second dichroic filter 53B to reflect blue light applied from the LED portion 51 to the condenser lens 15. The second dichroic filter 53B may, of course, be configured such that the angle can be freely adjusted to suit a position where the LED portion 51 is arranged.

As shown in FIG. 6, the filters of the RGB filter 60 and fluorescence observation filter 61 are fixed on the light entrance surface of the rotating plate main body 17A with adhesive or the like, like the first dichroic filter 53A.

A transmission characteristic of the first dichroic filter 53A and a reflectance characteristic of the second dichroic filter 53B are as shown in FIGS. 8 and 9, respectively.

More specifically, the first dichroic filter 53A has, as the transmission characteristic, the filter characteristic of transmitting light E1 in a wavelength band of, e.g., 400 to 470 nm (corresponding to the first wavelength band) and reflecting light in any other wavelength band, as shown in FIG. 8.

The second dichroic filter 53B has, as the reflectance characteristic, the filter characteristic of reflecting light E0 in a wavelength band of, e.g., 450 to 470 nm (corresponding to the first wavelength band) and transmitting light in any other wavelength band, as shown in FIG. 9.

Note that although the reflectance characteristic of the second dichroic filter 53B has been explained such that the second dichroic filter 53B reflects the light E0 in the wavelength band of 450 to 470 nm (corresponding to the first wavelength band), the present invention is not limited thereto, and the reflectance characteristic may be set such that light to be reflected is in a wavelength band which reverses dominance of one of the lamp 12 and the LED portion 51 over the other.

The transmission characteristic of the first dichroic filter 53A is, e.g., the transmission characteristic of transmitting the light E1 in the wavelength band of 400 to 470 nm. Since, of light from the lamp 12, light in the wavelength band of 450 to 470 nm is reflected by the second dichroic filter 53B and is hardly emitted toward the condenser lens 15. Accordingly, a transmission characteristic of the second dichroic filter 53B may be set to transmit light in a wavelength band of, e.g., 400 to 450 nm.

Although the blue LED 51A has been explained in the present embodiment as being an LED which is generally used in a projector or the like and emits the blue light E2 with a center wavelength near 460 nm, the present invention is not limited thereto. An LED which emits blue light with any other center wavelength may be used.

In the case, optical characteristics of the first dichroic filter 53A and second dichroic filter 53B may be determined according to the center wavelength of the blue LED 51A to be used.

For example, if the blue LED 51A with a center wavelength near 440 nm is used, the first dichroic filter 53A may be set to have, as the transmission characteristic, the filter characteristic of, e.g., transmitting light in a wavelength band of 400 to 470 nm and reflecting light in any other wavelength. The second dichroic filter 53B may be set to have, as the reflectance characteristic, the filter characteristic of, e.g., reflecting light in a wavelength band of 430 to 450 nm and transmitting light in any other wavelength.

With the above-described LED portion 51 and fluorescence observation optical device 53 of the light source device 3, light condensed by the condenser lens 15 at the time of fluorescence observation is excitation light EX with a wavelength as shown in FIG. 11, which is obtained by superimposing, e.g., the light E1 (see FIG. 8) with the wavelength band of 400 to 470 nm transmitted by the first dichroic filter 53A and the light E2 (see FIG. 9) with the wavelength band of 450 to 470 nm reflected by the second dichroic filter 53B on each other and has increased in amount.

Referring back to FIG. 1, illumination light from the light source device 3 is transmitted (guided) toward a distal end of the insertion portion 7 of the endoscope 2 by the light guide fiber 9. The light guide fiber 9 transmits light for fluorescence observation and light for normal observation with a small transmission loss. The light guide fiber 9 is made of, e.g., multi-component glass fibers or quartz fibers.

Light transmitted to a distal end surface of the light guide fiber 9 passes through an illumination lens 24 which is attached to an illumination window facing the distal end surface, spreads out, and is applied toward a part to be observed in a body cavity.

Note that the scope switch 29 for giving an instruction to choose between the fluorescence image mode and the normal image mode, a freeze instruction, and a release instruction is provided at the endoscope 2, an operation signal from the scope switch 29 is inputted to the control portion 37, and the control portion 37 performs control operation corresponding to the operation signal.

For example, if a normal mode switch of a mode selector switch in the scope switch 29 is operated, the light source device 3 enters a state of sequentially supplying illumination light for the normal mode, i.e., supplying R light, G light, and B light, and the processor 4 enters a state of performing signal processing corresponding to the normal mode.

On the other hand, if a fluorescence mode switch of the mode selector switch is operated, the light source device 3 enters a state of sequentially supplying illumination light for the fluorescence mode, i.e., R2 light, G2 light, and EX light (with the wavelength obtained after the superimposition shown in FIG. 11), and the processor 4 enters a state of performing signal processing corresponding to the fluorescence mode.

The fluorescence CCD 28a is driven by a CCD driving signal from the CCD driving portion 31 provided within the processor 4, photoelectrically converts an optical image formed at the fluorescence CCD 28a, and outputs an image signal. The normal CCD 28b is similarly driven by a CCD driving signal from the CCD driving portion 31 provided within the processor 4, photoelectrically converts an optical image formed at the normal CCD 28b, and outputs an image signal.

Which one of the image signals is to be outputted to the processor 4 is switched by the selector SW 46. An outputted image signal is amplified by the preamplifier 32 provided within the processor 4 and is further amplified to a predetermined level by an automatic gain control (AGC) circuit 33. The resultant signal is then converted from an analog signal into a digital signal (image data) by an A/D conversion circuit 34. Pieces of image data from the A/D conversion circuit 34 pass through a multiplexer 35 which switches an output destination and are temporarily stored in a first frame memory 36a, a second frame memory 36b, and a third frame memory 36c.

Note that the CCD driving portion 31 is controlled by the control portion 37.

The control portion 37 also controls the movement motor 20 in accordance with a selected one of the modes. The rotation motor 16 is controlled by the control portion 37, and an output from an encoder (not shown) attached to a rotating shaft or the like of the rotation motor 16 is inputted to the control portion 37. The control portion 37 controls the CCD driving portion 31, switching in the multiplexer 35, and the like in synchronization with the output from the encoder.

The control portion 37 controls switching in the multiplexer 35 and controls the multiplexer 35 in the normal mode such that pieces of image data picked up under illumination of the R, G, and B filters 60a, 60b, and 60c are sequentially stored in the first frame memory 36a, second frame memory 36b, and third frame memory 36c, respectively.

In the fluorescence mode, the control portion 37 controls switching in the multiplexer 35 and controls the multiplexer 35 such that signals obtained by image pickup under illumination of the R2 filter 61a, the G2 filter 61b, and the fluorescence observation optical device 53 are sequentially stored in the first frame memory 36a, second frame memory 36b, and third frame memory 36c, respectively.

Pieces of image data stored in the frame memories 36a to 36c are inputted to an image processing portion 38 and are subjected to edge enhancement and the like. The resultant pieces of data are converted into analog RGB signals by a D/A conversion circuit 39 and are outputted to the monitor 5.

A light control circuit 40 which automatically controls an aperture value of the light source diaphragm 13 within the light source device 3 on the basis of a signal having passed through the preamplifier 32 is also provided at the processor 4. The light control circuit 40 is controlled by the control portion 37.

The control portion 37 also controls a lamp current which lights and drives the lamp 12 of the lamp driving portion 11 and performs control operation corresponding to operation of the scope switch 29.

If the fluorescence mode is selected by operation of the scope switch 29, the control portion 37 drives the lamp driving portion 11 and outputs a signal indicating running in the fluorescence mode to the LED driving portion 52 shown in FIG. 1.

At the time, in the present embodiment, the switching filter 17 outputs, to the LED driving portion 52, a filter discrimination signal indicating which filter is located on an optical axis of light emitted from the lamp 12, in the light source device 3 shown in FIG. 1. That is, a filter discrimination signal is used to discriminate which one of the R2 filter 61a and G2 filter 61b of the fluorescence observation filter 61 and the fluorescence observation optical device 53 or the R filter 60a, G filter 60b, and B filter 60c of the RGB filter 60 for normal observation is located on the optical axis.

The light source diaphragm 13 outputs a POT signal indicating a diaphragm aperture to the LED driving portion 52.

Note that the POT signal is a 8-bit digital signal which is outputted to be "255" when the light source diaphragm 13 is fully open and is outputted to be "0" when the light source diaphragm 13 is fully closed.

The LED driving portion 52 determines a lighting time $T_{ON}$ for the blue LED 51A corresponding to an inputted POT signal to suit an opening characteristic of the light source diaphragm 13 and controls the blue LED 51A to light up during the lighting time $T_{ON}$.

Note that an example of the lighting time $T_{ON}$ for the blue LED 51A corresponding to a POT signal determined by the LED driving portion 52 is shown in FIG. 12. That is, the LED driving portion 52 controls lighting of the blue LED 51A using the lighting time $T_{ON}$ corresponding to an inputted POT signal, as shown in FIG. 12.

Operation of the present embodiment with the above-described configuration will be described below.

As shown in FIG. 1, the light source connector 10 of the endoscope 2 is connected to the light source device 3, and a signal connector (not shown) of the endoscope 2 is connected to the processor 4. The endoscope apparatus 1 is placed in a connection state as shown in FIG. 1, and the devices are powered on and are placed in an operating state.

The control portion 37 then performs initialization operation and performs control to set the endoscope apparatus 1 to run in, e.g., the normal mode in an initialized state.

For the normal mode, the control portion 37 controls the movement motor 20 of the light source device 3 and sets the switching filter 17 such that the RGB filter 60 on the outer peripheral side is located in the illumination optical path.

The rotation motor 16 is then rotated. The R, G, and B filters 60a, 60b, and 60c of the switching filter 17 are sequentially located in the illumination optical path of white light from the lamp 12, and R illumination light, G illumination light, and B illumination light are emitted toward an object to be observed.

Signals obtained after image pickup by the normal CCD 28b under illumination with the R light, G light, and B light are amplified and A/D-converted. A state of the multiplexer 35 is sequentially switched by the control portion 37, and the signals are sequentially stored in the first frame memory 36a, second frame memory 36b, and third frame memory 36c.

Pieces of image data for R, G, and B color components stored in the frame memories 36a to 36c are simultaneously read out in a predetermined frame period (e.g., 33 ms, in other words, 1/30 sec) and are subjected to edge enhancement and the like in the image processing portion 38. The resultant pieces of image data pass through the D/A conversion circuit 39, are converted into standard analog signals, in the case, RGB signals, and are outputted to the monitor 5. A normal observation image (reflecting a color tone of a subject when the subject is directly observed with applied white light) is displayed in color on a display surface of the monitor 5.

In the above-described manner, a subject is observed in the normal mode. For example, if it is desired to perform fluorescence observation on a subject such as a diseased part of interest, the fluorescence mode switch of the mode selector switch of the scope switch 29 is operated.

Upon receipt of an operation signal from the fluorescence mode switch, the control portion 37 drives the movement motor 20 to move the switching filter 17, sets the switching filter 17 such that the fluorescence observation filter 61 and fluorescence observation optical device 53 are located on the illumination optical path, and switches the endoscope apparatus 1 to the fluorescence mode.

When an operating mode is set to the fluorescence mode, illumination light for the fluorescence mode, i.e., excitation light (EX), G2 light, and R2 light shown in FIG. 13 are sequentially supplied to the light guide fiber 9 of the endoscope 2, and the excitation light (EX), G2 light, and R2 light are sequentially applied to a subject.

When the excitation light (EX) is applied, the LED driving portion 52 is supplied with a filter discrimination signal from the switching filter 17, as shown in FIG. 13. The LED driving portion 52 detects, from the filter discrimination signal, the timing when the fluorescence observation optical device 53 serving as an excitation light (EX) filter is located on the optical axis and lights the blue LED 51A for the lighting time $T_{ON}$ corresponding to a POT signal as shown in FIG. 12 (see FIG. 13).

The excitation light at the time is excitation light with a wavelength as shown in FIG. 11 which is obtained by superimposing, e.g., the light (see FIG. 8) with the wavelength of 400 to 470 nm transmitted by the first dichroic filter 53A and the light (see FIG. 9) with the wavelength of 450 to 470 nm reflected by the second dichroic filter 53B on each other by the LED portion 51 and fluorescence observation optical device 53 and has increased in amount, as described above.

This makes it possible to provide a good balance between application of excitation light (EX light on a short wavelength side), G2 light, and R2 light applied from the lamp 12 and application of excitation light (EX light on a long wavelength side) applied from the blue LED 51A of the LED portion 51. That is, it is possible to perform control of light from the blue LED 51A in conjunction with the lamp 12 in the fluorescence mode and increase the amount of excitation light at the time.

As described above, excitation light (EX), G2 light, and R2 light are sequentially applied to a subject. When R2 (or G2) is applied, same operation as in a case where R light (or G light) is applied in the normal mode is performed. That is, in this case, light obtained after R2 (or G2) is reflected by the subject is received by the fluorescence CCD 28a. The fluorescence CCD 28a picks up an image without being affected by the excitation light cut-off filter 27a.

On the other hand, when excitation light (EX) is applied, reflected light of the excitation light (EX) is almost completely cut off by the excitation light cut-off filter 27a, and fluorescence in a transmission band of the excitation light cut-off filter 27a is received from the subject side.

Intensity of the fluorescence is much lower than intensity of the light obtained after R2 (or G2) is reflected by the subject. Accordingly, operation similar to the above-described application of R, G or B in the normal mode and signal processing for each case is performed such that a bright fluorescence image (which can be easily compared with an image of light obtained after R2 (or G2) is reflected by the subject) is displayed.

If an image of light obtained after R2 (or G2) is reflected by a subject is to be picked up, image data picked up by the fluorescence CCD 28a only during a part of an illumination period is stored in the first frame memory 36a (or second frame memory 36b).

If excitation light (EX) is applied, and a fluorescence image of the excitation light is to be picked up, the amount of excitation light (EX) as illumination light is increased under control of the LED driving portion 52, as described above. Fluorescence image data picked up in this case is stored in the third frame memory 36c.

Pieces of image data in the first frame memory 36a to third frame memory 36c are simultaneously read out with a frame period and are displayed in, e.g., pseudo color on the monitor 5.

In the above-described manner, a bright fluorescence image with a high S/N ratio is obtained even in the fluorescence mode.

With a fluorescence image obtained in the fluorescence mode, it is possible to obtain an image which allows easy distinction between a normal tissue and a cancerous tissue and an image which allows easy judgment as to whether there is an inflammatory part.

According to the present embodiment, the LED portion 51 as the second light source and the fluorescence observation optical device 53 on the switching filter 17 are provided within the light source device 3 without providing a blue LED at a distal end portion as in the related art. Since power of the LED need not be limited in consideration of an influence of heat generation in a living body, it is possible to increase the amount of excitation light and perform high-accuracy fluorescence observation.

Assume that excitation light is applied to a living body. Ultraviolet light as the excitation light can be applied only to a tissue near a surface of the living body while blue light as the excitation light can be applied to a deeper tissue.

Note that a configuration in which the fluorescence observation optical device 53 is provided at the switching filter 17 of the rotating plate has been described in the present embodiment. Since weight of the fluorescence observation optical device 53 is relatively heavy, the weight is expected to affect rotational operation of the switching filter 17. In the present embodiment, a rotation correction member such as a weight may be optimally arranged such that a barycenter of the switching filter 17 is in a center. This prevents nonuniformity in rotation of the switching filter 17 and allows satisfactory rotation.

The present invention is not limited to the above-described embodiment and modification, and various modifications may be made without departing from scope of the invention.

What is claimed is:

1. A light source device comprising:
a first light source which emits illumination light whose wavelength band covers a first wavelength band and a second wavelength band;
a light condensing portion which is arranged on an optical axis of illumination light emitted from the first light source and condenses light;
a rotating plate which has a first window portion that transmits illumination light in the first wavelength band and a second window portion that transmits at least illumination light in the second wavelength band and is rotatably arranged such that the first window portion and the second window portion pass through the optical axis of the illumination light;
a driving control portion which controls rotation of the rotating plate;
a second light source which emits illumination light in the first wavelength band toward the rotating plate; and
an optical device which is arranged at the rotating plate, can transmit the illumination light emitted from the first light source, and can reflect the illumination light emitted from the second light source to the light condensing portion, wherein
the optical device has a first dichroic filter and a second dichroic filter which are formed integrally with the first window portion, the first dichroic filter has a transmission characteristic of being able to transmit illumination light in the first wavelength band emitted from the first light source, and the second dichroic filter has a reflectance characteristic of reflecting illumination light emitted from the second light source to the light condensing portion.

2. The light source device according to claim 1, wherein the rotating plate has a third window portion which transmits illumination light in a third wavelength band at a position off a rotational trajectory of the first window portion and the second window portion, and
the device further comprises a movement mechanism which moves the rotating plate between a first position where the first window portion and the second window portion can pass through the optical axis of the illumination light emitted from the first light source and a second position where the third window portion can pass through the optical axis.

3. An endoscope apparatus comprising:
a light source device including a first light source which emits illumination light whose wavelength band covers a first wavelength band and a second wavelength band, a light condensing portion which is arranged on an optical axis of illumination light emitted from the first light source and condenses light, a rotating plate which has a first window portion that transmits illumination light in the first wavelength band and a second window portion that transmits at least illumination light in the second wavelength band and is rotatably arranged such that the first window portion and the second window portion pass through the optical axis of the illumination light, a driving control portion which controls rotation of the rotating plate, a second light source which emits illumination light in the first wavelength band toward the rotating plate, and an optical device which is arranged at the rotating plate, can transmit the illumination light emitted from the first light source, and can reflect the illumination light emitted from the second light source to the light condensing portion; and
an endoscope including a distal end portion including an observation optical system which applies light from the condensing portion of the light source device to a subject and an image pickup optical system which picks up an image of the subject, and an insertion portion which is connected to the distal end portion on an insertion direction proximal end side, wherein
the optical device has a first dichroic filter and a second dichroic filter which are formed integrally with the first window portion, the first dichroic filter has a transmission characteristic of being able to transmit illumination light in the first wavelength band emitted from the first light source, and the second dichroic filter has a reflectance characteristic of reflecting illumination light emitted from the second light source to the light condensing portion.

* * * * *